United States Patent [19]

Smith

[11] Patent Number: 5,028,235

[45] Date of Patent: Jul. 2, 1991

[54] METHOD OF MAKING A FALSE TOOTH

[76] Inventor: Avis J. Smith, 380 Cozine Ave. - Apt. 4A, Brooklyn, N.Y. 11207

[21] Appl. No.: 397,894

[22] Filed: Aug. 24, 1989

[51] Int. Cl.⁵ .............................................. A61C 5/10
[52] U.S. Cl. ................................... 433/223; 434/263; 433/218; 433/213
[58] Field of Search ....................... 433/223, 218, 213; 434/263

[56] References Cited

U.S. PATENT DOCUMENTS

| | | | |
|---|---|---|---|
| 884,977 | 4/1908 | Boos | 433/218 X |
| 2,674,802 | 4/1954 | Williams | 434/263 |
| 2,930,125 | 3/1960 | Pos | 433/223 |
| 3,458,936 | 8/1969 | Schulz et al. | 434/263 |
| 3,483,618 | 12/1969 | Andrew | 433/223 |
| 4,355,978 | 10/1982 | Ericson | 433/223 X |
| 4,770,637 | 9/1988 | Harvell, Jr. | 434/263 |

FOREIGN PATENT DOCUMENTS 3318069 11/1984 Fed. Rep. of Germany ...... 434/263

Primary Examiner—Robert P. Swiatek
Assistant Examiner—Nicholas D. Lucchesi
Attorney, Agent, or Firm—Charles E. Baxley

[57] ABSTRACT

A false tooth is made by first making a base that may correspond to the patient's mouth but that has no crown, then modeling a plurality of separate crown pieces that interfit complementarily to form a crown, and finally anchoring the pieces so that they form a complete crown atop the base.

2 Claims, 1 Drawing Sheet

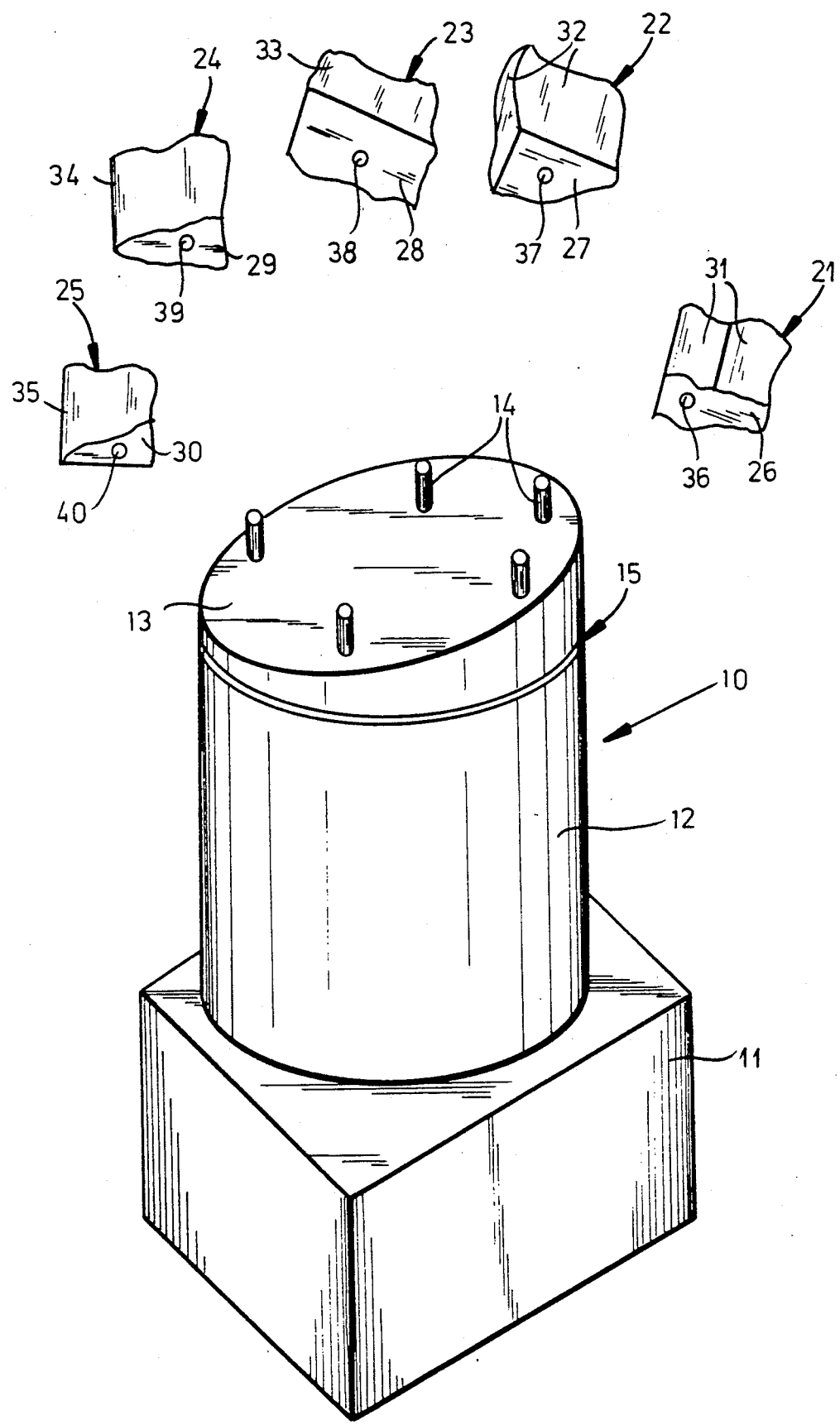

METHOD OF MAKING A FALSE TOOTH

FIELD OF THE INVENTION

The present invention relates to making a false tooth. More particularly this invention concerns a method of teaching the fabrication of a false tooth.

BACKGROUND OF THE INVENTION

A standard false tooth is made by making a positive primary mold from the patient's mouth from which it is cast from wax a base corresponding to the part of the tooth that is to fit in the vacant space in the patient's mouth. On the top of this base the crown of the tooth must be modeled by the dental technician in a shape that will coact with the opposing tooth or teeth and that will look normal. The finished model is then used to make another mold, typically from plaster, and the tooth is then investment cast, usually of a porcelain material for best appearance.

Shaping the top part of the tooth is an extremely difficult procedure bordering on an artistic endeavor. It takes considerable practice to produce a usable crown by a procedure that is more akin to sculpture than dentistry. Thus a dental student must spend a very many hours painstakingly constructing teeth of wax to master the basic elements of the procedure.

It is known for example from U.S. Pat. Nos. 424,050 and 4,206,545 to make up a crown from a decorative porcelain side piece and from a metal cap, but the model for such a crown is apparently modeled in the standard manner. Similarly U.S. Pat. No. 4,778,386 describes a two-part crown, but gives no hint as to how to model it.

OBJECTS OF THE INVENTION

It is therefore an object of the present invention to provide an improved method both of making a false tooth and of teaching how to make such a false tooth.

Another object is the provision of such an improved method both of making a false tooth and of teaching how to make such a false tooth which overcomes the above-given disadvantages, that is which makes the learning and manufacture processes both easier.

SUMMARY OF THE INVENTION

A method of making a model of a false tooth according to this invention comprises the steps of first making a base that may correspond to the patient's mouth but that has no crown, then modeling a plurality of separate crown pieces that interfit complementarily to form a crown, and finally anchoring the pieces so that they form a complete crown atop the base.

With this procedure the students can concentrate on the formation of the individual prominences and recesses of the crown one at a time, making it much easier how to sculpt the parts. The pieces can then be assembled and, if necessary, any single piece can be reworked or redone. The subdivision of the crown can follow the standard clefts and ridges of the tooth to be made.

According to this invention the base is provided with a respective upstanding anchor pin for each of the pieces and the pieces are each formed with a hole complementary to the respective upstanding pin. Thus the pieces are anchored by fitting the holes over the respective pins.

The pieces according to this invention are modeled from wax. Thus the finished model can be used in an investment casting method in the standard procedure.

DESCRIPTION OF THE DRAWINGS

The above and other objects, features, and advantages will become more readily apparent from the following, reference being made to the accompanying drawing whose sole figure is an exploded perspective view of a modeled tooth according to this invention.

DETAILED DESCRIPTION OF THE PREFERRED EMBODIMENT

As seen in the drawing a tooth base 10 fashioned of standard investment wax can have a parallepipedal base 11 and a generally cylindrical projection 12 that eventually is shaped to correspond to the root. This projection 12 has an upper surface 13 that is generally planar and that is here provided with five parallel and upstanding metal pins 14. Immediately below the surface 13 the projection 12 is formed with a groove 15 that delimits the crown part from the root part of the tooth to be modeled.

The crown here is formed by five different pieces 21, 22, 23, 24, and 25 each having an upper side corresponding to a portion of the anatomical crown surface to be formed, a planar lower side 26, 27, 28, 29, and 30 and side surfaces 31, 32, 33, 34, and 35 that fit together. In addition each of the bottom faces 26, 27, 28, 29, and 30 is formed with a respective hole 36, 37, 38, 39, and 40 that is meant to receive the respective pin 14.

These pieces 21, 22, 23, 24, and 25 are formed separately so that the students can concentrate on the individual parts of the crown. Then they are assembled on the surface 13 with the side surfaces 31, 32, 33, 34, and 35 engaging one another. The resultant crown can be modeled further if necessary or can be immediately used for investment casting in accordance with standard procedures.

I claim:

1. A method of making a false tooth, the method comprising the steps of:
   providing a base corresponding to a patient's mouth and having a planar upper surface and a plurality of spaced parallel anchor pins upstanding from and perpendicular to said upper surface at locations corresponding to the entirety of the patient's tooth that is to be replaced;
   providing a plurality of separate crown pieces molded from wax and having side surfaces complementarily interfittable with each other to form a crown and having planar bottom faces each with a single hold perpendicular thereto for receiving a corresponding particular one of said anchor pins; and
   assembling said crown pieces with said hole of each said crown piece receiving its said corresponding particular one of said anchor pins while interfitting said side surfaces of said crown pieces together.

2. The method defined in claim 1 performed in dental laboratory education.

* * * * *